United States Patent [19]
Derleth et al.

[11] Patent Number: 5,315,051
[45] Date of Patent: May 24, 1994

[54] PROCESS FOR THE OXYCHLORINATION OF ETHYLENE AND CATALYST COMPOSITIONS FOR THE OXYCHLORINATION

[75] Inventors: Helmut Derleth, Nienburg; Robert Walter, Langenhagen; Günter Weidenbach, Hanover, all of Fed. Rep. of Germany; Michel Strebelle, Brussels, Belgium

[73] Assignee: Solvay (Société Anonyme), Brussels, Belgium

[21] Appl. No.: 427,492

[22] Filed: Oct. 27, 1989

Related U.S. Application Data

[63] Continuation of Ser. No. 67,250, Jun. 26, 1987, Pat. No. 4,910,354.

[30] Foreign Application Priority Data

Jun. 27, 1986 [FR] France .................... 86 09504

[51] Int. Cl.$^5$ .................................. C07C 17/156
[52] U.S. Cl. .................................. 570/245; 570/243; 502/225
[58] Field of Search ................. 570/243, 245; 502/225

[56] References Cited

U.S. PATENT DOCUMENTS

| | | | |
|---|---|---|---|
| 3,468,968 | 9/1969 | Baker et al. | |
| 3,624,170 | 11/1971 | Wakiyama et al. | 570/245 |
| 4,069,170 | 1/1978 | Blake et al. | 570/243 |
| 4,124,534 | 11/1978 | Leitert et al. | 570/224 |
| 4,382,021 | 5/1983 | Laurer et al. | 570/243 |
| 4,446,249 | 5/1984 | Eden | 502/225 |
| 4,460,699 | 7/1984 | Convers et al. | 570/243 |
| 4,910,354 | 3/1990 | Derleth et al. | 570/243 |
| 5,227,548 | 6/1993 | Scott | 570/245 |

FOREIGN PATENT DOCUMENTS

| | | | |
|---|---|---|---|
| 1352448 | 1/1964 | France . | |
| 2095351 | 2/1972 | France . | |
| 43-003761 | 2/1968 | Japan | 570/243 |
| 46-040251 | 11/1971 | Japan . | |
| 958458 | 5/1964 | United Kingdom | 570/243 |
| 969937 | 9/1964 | United Kingdom . | |

*Primary Examiner*—Anthony Green
*Attorney, Agent, or Firm*—Spencer, Frank & Schneider

[57] ABSTRACT

The invention relates to a process for the oxychlorination of ethylene by means of a catalyst composition comprising an alumina support impregnated with cupric chloride, magnesium chloride and a chloride of an alkali metal chosen from sodium and lithium. The oxychlorination performed in this manner makes it possible to obtain an excellent yield without the reactor being corroded by the catalyst composition employed.

14 Claims, 6 Drawing Sheets

PROCESS FOR THE OXYCHLORINATION OF ETHYLENE AND CATALYST COMPOSITIONS FOR THE OXYCHLORINATION

This is a continuation of application Ser. No. 07/067,250 filed Jun. 26, 1987 now U.S. Pat. No. 4,910,354 the entire specification of which is incorporated herein by reference.

FIELD OF THE INVENTION

The present invention relates to a process for the oxychlorination of ethylene with the use of a catalyst composition permitting an improved yield to be obtained and simultaneously giving rise to a reduced corrosion effect in stainless steel reactors, particularly through a reduction in the adhesion and lumping of the catalyst particles.

TECHNOLOGY REVIEW

Chlorination of gaseous hydrocarbons with the use of hydrogen chloride and air or oxygen is an operation which has been known for a long time. This chlorination is usually carried out in the presence of catalysts consisting of metal salts deposited on inert supports. The metal salts which are generally employed are halides such as cupric chloride which, when employed by itself, has nevertheless the disadvantage of being relatively voltatile, and this results in a drop in catalytic activity and in the yield of the oxychlorination reaction, which is industrially unacceptable, when this compound is employed in a fluidized bed in an industrial plant.

To overcome these disadvantages it has been proposed to incorporate into the catalyst compositions other metal salts such as the chlorides of alkali and alkaline-earth metals and of other metals derived from the rare earths or lanthanides (British Patent GB-969,937, Belgian Patent BE-741,055).

These various catalyst compositions have activities which depend in particular on the nature of the hydrocarbon which is to be used and the nature of the metal salt or salts added to reduce the effects of the volatility of cupric chloride. Furthermore, these various catalyst compositions also give rise to corrosive action on the steel of industrial reactors, due in particular to the adhesion and lumping of the catalyst particles on the walls. This corrosion is one of the effects which, in the present state of knowledge, cannot be deduced either qualitatively or quantitatively from the technical data relating to the nature of the salts used, and which must be investigated empirically in the case of each catalyst composition which is envisaged.

SUMMARY OF THE INVENTION

Copper- and magnesium-based catalyst compositions have now been found, which make it possible to manufacture 1,2-dichloroethane by the oxychlorination of ethylene, with an activity and a yield which have never been reached industrially with compositions containing these two metals. At the same time, these compositions give rise to minimum adhesion and lumping of the catalyst particles, as well as minimum corrosion of the industrial reactor.

BRIEF DESCRIPTION OF THE DRAWINGS

FIGS. 1, 2 and 3 illustrate a weak and acceptable steel corrosion. On the other hand, FIG. 4 illustrates a high and industrially unacceptable steel corrosion.

FIG. 9 illustrates that when operating above a certain lithium limit, unacceptable adhesion and lumping of catalyst particles occurs. FIGS. 10 and 12 illustrate that when the lithium limits of the catalysts of the invention are exceeded, high adhesion and high lumping are obtained, and this makes corrosion measurements in an erosimeter impossible (FIG. 11 and FIG. 13).

DETAILED DESCRIPTION OF THE INVENTION

Figure 1:
FIGS. 1 to 4 illustrate corrosion of stainless steel reactors in which four tests were carried out using catalyst compositions containing different quantities of sodium, as shown in Table 1 below.

Consequently, the present invention relates to a process for the oxychlorination of ethylene to 1,2-dichloroethane, in which the oxychlorination reaction is catalysed by a catalyst composition comprising an alumina support on which there are deposited cupric chloride, magnesium chloride and an alkali metal chloride chosen from sodium chloride and lithium chloride.

When the alkali metal employed is sodium, the operation is preferably carried out with atomic ratios of copper salts to sodium salts of 1:0.01–0.2. It has been found, in fact, that in the case of sodium salts, corrosion of stainless steel reactors is observed, and this becomes considerable or even unacceptable when Cu:Na atomic ratios of 1:0.2 are exceeded.

On the other hand, when the alkali metal is lithium, the atomic ratio Cu:Li is less critical and it is possible to operate with Cu:Li ratios ranging from 1:0.0001 to 1:2.

The invention also relates to catalyst compositions for the oxychlorination of hydrocarbons comprising either 1) cupric chloride, magnesium chloride and NaCl in atomic ratios of between 1:0.1–1.5:0.01–0.2, deposited on alumina, or
2) cupric chloride, magnesium chloride and LiCl, deposited on alumina. In this case, the ratios of the various salts are usually between 1:0.1–1.5:0.00-01–1.5 and preferably between 1:0.3–1:0.001–1.

The alumina employed in the catalyst compositions of the invention may be of any provenance and may be produced by any known process: eta- or gamma- type aluminas are usually employed. Good results have been obtained with a gamma-type alumina.

The alumina generally employed in the catalyst compositions of the invention has a mean particle diameter of between 20 and 100 μm and preferably a mean diameter of between 25 and 75 μm.

The specific surface of the alumina, measured according to the B.E.T. method, is generally between 50 $m^2/g$ and 250 $m^2/g$. Good results have been obtained with an alumina having a specific surface between 100 $m^2/g$ and 210 $m^2/g$.

Lastly, the pore volume of the aluminas usually employed lies between 0.1 and 1 $cm^3/g$. The pore volume is preferably between 0.2 and 0.8 $cm^3/g$ and good results have been obtained with an alumina having a pore volume between 0.3 and 0.6 $cm^3/g$.

It should be noted that alumina naturally contains a greater or lesser quantity of sodium atoms which may be integrated into the crystalline lattice or may be bonded in any chemical form. The presence of these sodium atoms, which may be described more conveniently as "unwashable sodium atoms", is of no importance for the present invention, which relates solely to catalyst compositions which contain an alkali metal, in salt form, which can be considered as being a "washable alkali metal". These alkali metal salts are not bonded chemically to the alumina support and are generally introduced into the catalyst compositions by impregnating the alumina with the salt in question. This impregnation with the alkali metal salt required may be carried out either at the same time as impregnation with the other salts, or before, or after this impregnation.

The way in which the catalyst compositions according to the invention are produced is not critical per se, provided that the catalyst compositions finally obtained correspond to the characteristics described above. A preparative method which has produced good results consists in impregnating a γ alumina having the following characteristics:

means particle diameter of approximately 50 μm,
B.E.T. specific surface of between 170 and 190 m$^2$/g,
pore volume of between 0.4 cm$^3$/g, and
free-flow packing density of 0.75 kg/dm$^3$.

The impregnation is carried out in a single step at a temperature of 75° C. with an aqueous solution containing the required quantities of copper, magnesium and alkali metal chlorides. The appearance of a liquid phase which is not adsorbed by the solid is avoided by restricting the volume of the impregnating solution to 70 to 100% of the pore volume of the quantity of alumina employed. This impregnated alumina is then dried before being introduced into the oxychlorination reactor as such.

The catalyst compositions finally employed in the oxychlorination process generally have a copper content, calculated as metal, of between 30 g/kg and 90 g/kg. This quantity preferably lies between 50 and 75 g/kg and catalyst compositions which are most particularly preferred are those having a copper content lies between 60 and 70 g/kg.

The content of the other salts in the catalyst compositions can, in its turn, be readily deduced from the copper contents specified in this manner together with the atomic ratios already detailed above.

The final catalyst compositions generally have a B.E.T. specific surface of between 25 m$^2$/g and 200 m$^2$/g and preferably between 50 and 150 m$^2$/g. Good results have been obtained with catalyst compositions whose B.E.T. specific surface between 100 and 140 m$^2$/g.

The catalyst compositions may be employed in any oxychlorination process carried out with a catalyst arranged in a stationary bed or a fluidized bed. They are particularly advantageous in a process in which the catalyst is in the form of a fluidized bed, because of an improved yield and because of the absence of corrosion in stainless steel reactors.

When the operation is carried out with a catalyst arranged in a fluidized bed, the temperature at which the oxychlorination reaction takes place is usually between 200° and 300° C. Preferably, this temperature lies between 220° and 280° C. Lastly, good results have been obtained with a temperature situated in the region of 240° C.–270° C.

The pressure at which the oxychlorination reaction is performed is not critical in itself. Usually, the operation is carried out using pressures of between 1 and 10 atm and preferably using pressures of between 1 and 8 atm.

The fluidization velocity of the catalyst compositions is not critical in itself and depends essentially on the particle size distribution of the catalyst and on the size of the apparatus. In general, the operation is carried out using velocities of between 5 and 100 cm/s and preferably between 10 cm/s and 50 cm/s.

Lastly, the reactant ratio which is used is the same as that generally employed in earlier processes. The operation is customarily carried out with a slight excess of ethylene relative to the quantity of HCl employed. However, the catalyst compositions of the invention also make it possible to work in the vicinity of stoichiometry, or even excess of HCl.

The invention is more fully illustrated by the examples which follow.

EXAMPLE 1

225 cm$^3$ of a catalyst composition consisting of a gamma-type alumina, having a mean specific surface of 190 m$^2$/g, impregnated with an aqueous solution of copper, magnesium and sodium chlorides, are arranged, after drying, in a reactor made of Inconel 600, for fluid bed oxychlorination of ethylene to 1,2-dichloroethane, and equipped with small plates made of AISI type 316L austenitic stainless alloy.

In this reactor, the reactant gases are introduced via the bottom through a sintered metal filter. The reaction products are then depressurized to atmospheric pressure by a reactor pressure control valve. The reaction products are then cooled in a trap maintained at −20° C. and the uncondensed gases are washed in a water scrubber before sweeping over a sampling bulb. The balance of the products formed is established from chromatographic analyses of the liquid and gaseous products collected and from acidimetric titration of the aqueous solution collected at the foot of the scrubber.

4 tests are carried out using catalyst compositions containing different quantities of sodium, such as are shown in Table 1 below. This Table 1 also includes the reactor operating conditions and the results obtained.

The yields obtained in these laboratory trials are limited by the residence time, restricted to 5 s. The conversion of C$_2$H$_4$ is consequently limited in all the trials (the operating conditions of an industrial reactor make it possible to reach residence times which are markedly longer: 10 to 80 s, and in most cases from 20 to 50 s, in order to ensure better ethylene conversion).

TABLE 1

| TEST | 1 | 2 | 3 | 4 |
|---|---|---|---|---|
| I. Catalyst | | | | |
| a) support: alumina: | | | | |
| type | γ | γ | γ | γ |
| specific surface (m$^2$/g) | 190 | 190 | 186 | 190 |
| b) catalyst composition | | | | |
| Cu in g/kg | 57 | 60 | 58 | 58.5 |
| Mg in g/kg | 16.5 | 17 | 17.7 | 16.2 |
| Na in g/kg | 0.1 | 1.0 | 1.7 | 6.2 |
| BET specific surface m$^2$/g | 120 | 122 | 124 | 113 |
| II. Operating conditions for the oxychlorination | | | | |
| HCl: Nl/h | 160 | 160 | 160 | 160 |
| air: Nl/h | 260 | 260 | 260 | 260 |
| C$_2$H$_4$: Nl/h | 84 | 84 | 84 | 84 |

TABLE 1-continued

Figure 2:
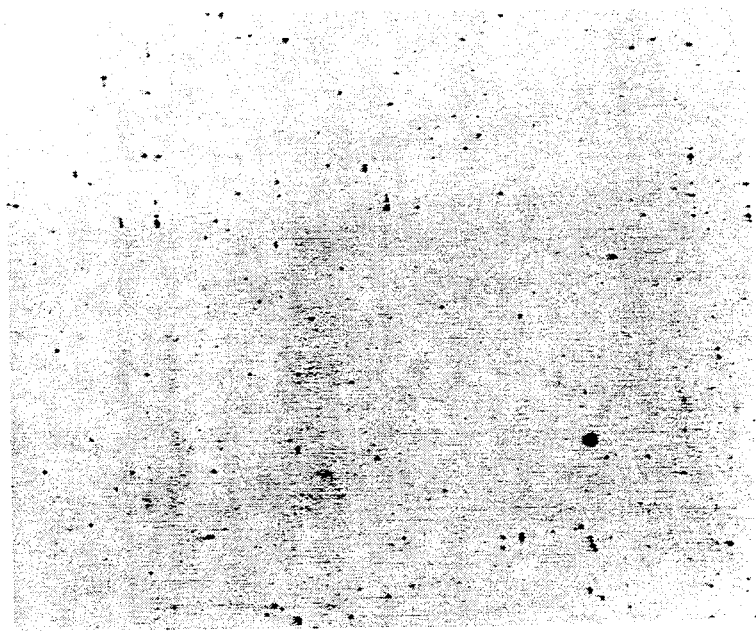
Figure 3:
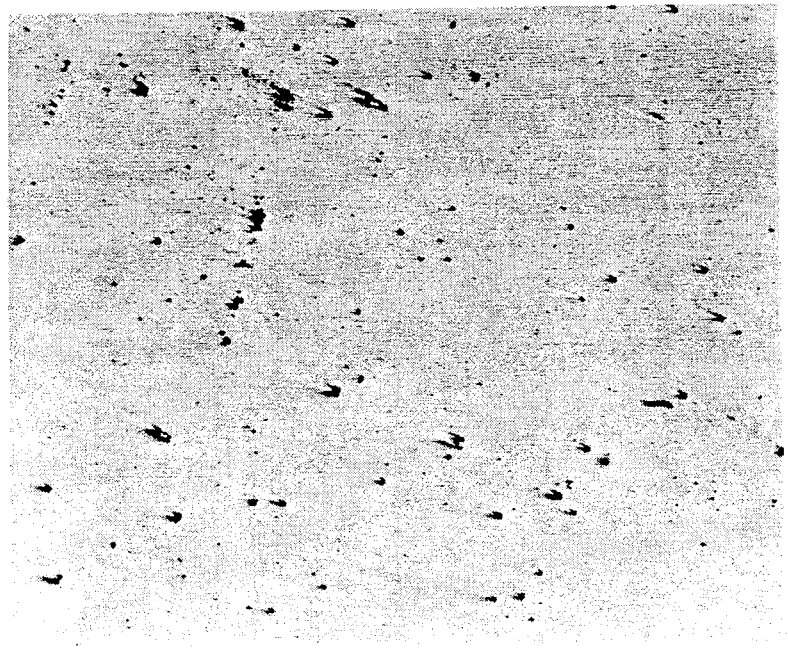
Figure 4:
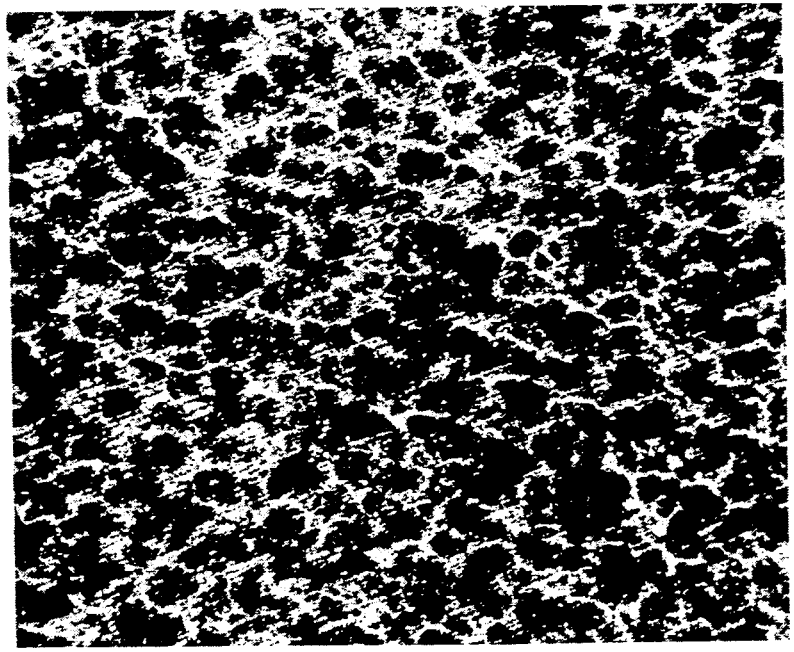

| TEST | 1 | 2 | 3 | 4 |
|---|---|---|---|---|
| t°: °C.* | 255 | 255 | 255 | 255 |
| pressure: bars absolute | 6 | 6 | 6 | 6 |
| fluidization velocity (cm/s) | 10 | 10 | 10 | 10 |
| contact time: s | 5 | 5 | 5 | 5 |
| YIELD: 1,2-DCE (mol %) | | | | |
| $C_2H_4$ employed | 90.5 | 91.5 | 91.8 | 91.8 |
| $C_2H_4$ conversion mol % | 95.5 | 96 | 96 | 95 |
| Formation of: | | | | |
| $C_2H_5Cl$ mol % based on the $C_2H_4$ employed | 1.6 | 0.6 | 0.5 | 0.6 |
| Corrosion of AISI 316 L steel | weak (FIG. 1) | weak (FIG. 2) | weak (FIG. 3) | strong (FIG. 4) |

*Stable temperature profile in the reactor: the temperature of the fluid bed does not deviate by more than 2° C. from average temperature.

From the comparison of the results of the various tests it may be concluded that:
- when operating *below* the sodium limits of the present invention (test 1), the yield of 1,2-dichloroethane is lower than that obtained with the catalyst compositions of the invention (tests 2 and 3). On the other hand, the steel corrosion is weak and acceptable;
- when operating *above* the sodium limits of the present invention (test 4) the yield of 1,2-dichloroethane is excellent and comparable to that obtained according to the invention (tests 2 and 3). On the other hand, the steel corrosion is high and thus unacceptable from an industrial standpoint;
- when operating within the sodium limits of the present invention (tests 2 and 3), an excellent yield of 1,2-dichloroethane and a weak and acceptable steel corrosion are observed at the same time.

EXAMPLE 2

225 cm³ of a catalyst composition consisting of a gamma-type alumina, having a mean specific surface of 180 to 190 m²/g, impregnated with an aqueous solution of copper, magnesium and lithium chlorides, are arranged, after drying, in a reactor made of Inconel 600, for fluid bed oxychlorination of ethylene to 1,2-dichloroethane, and equipped with small plates made of AISI type 316L austenitic stainless alloy.

In this reactor, the reactant gases are introduced via the bottom through a sintered metal filter. The reaction products are then depressurized to atmospheric pressure by a reactor pressure control value. The reaction products are then cooled in a trap maintained at −20° C. and the uncondensed gases are washed in a water scrubber before sweeping over a sampling bulb. The balance of the products formed is established from chromatographic analyses of the liquid and gaseous products collected and from acidimetric titration of the aqueous solution collected at the foot of the scrubber.

6 tests are carried out with catalyst compositions containing various quantities of lithium such as are given in Table 2 below. This Table 2 also includes the reactor operating conditions and the results obtained.

The yields obtained in these laboratory trials are limited by the residence time, restricted to 5 s. The conversion of $C_2H_4$ is consequently limited in all the trials (the operating conditions of an industrial reactor make it possible to reach residence times which are markedly longer: 10 to 80 s, and in most cases from 20 to 50 s, in order to ensure better ethylene conversion).

TABLE 2

| TEST | 5 | 6 | 7 | 8 | 9 | 10 |
|---|---|---|---|---|---|---|
| I. Catalyst | | | | | | |
| a) support: alumina: | | | | | | |
| type | γ | γ | γ | γ | γ | γ |
| specific surface (m²/g) | 190 | 190 | 180 | 180 | 180 | 180 |
| b) catalyst composition | | | | | | |
| Cu in g/kg | 59 | 60 | 59.6 | 58.1 | 56.5 | 56.9 |
| Mg in g/kg | 16.6 | 16.1 | 16.1 | 16.2 | 13.6 | 14.5 |
| Li in g/kg | 0.3 | 1 | 2.1 | 4.2 | 11.2 | 21.4 |
| BET specific surface m²/g | 117 | 123 | 99 | 94 | 88 | 67 |
| II. Operating conditions for the oxychlorination | | | | | | |
| HCl: Nl/h | 160 | 160 | 160 | 160 | 160 | 160 |
| air: Nl/h | 260 | 260 | 260 | 260 | 260 | 260 |
| $C_2H_4$: Nl/h | 84 | 84 | 84 | 84 | 84 | 84 |
| t°: °C.* | 255 | 255 | 255 | 255 | 255 | 255 |
| pressure: bars absolute | 6 | 6 | 6 | 6 | 6 | 6 |
| fluidization velocity (cm/s) | 10 | 10 | 10 | 10 | 10 | 10 |
| contact time: s | 5 | 5 | 5 | 5 | 5 | 5 |
| YIELD: 1,2-DCE (mol %) | | | | | | |
| $C_2H_4$ employed | 91.5 | 91.6 | 91.7 | 88 | 83 | nd |
| $C_2H_4$ conversion mol % | 97 | 96.4 | 95.4 | 91.2 | 88 | nd |
| Formation of: | | | | | | |
| $C_2H_5Cl$ mol % based on the $C_2H_4$ employed | 0.7 | 0.6 | 1.15 | 2.25 | 3.25 | — |
| Corrosion of | weak | weak | weak | weak | — | — |

TABLE 2-continued

Figure 5:
FIGS. 5 to 13 also illustrate corrosion of stainless steel reactors (AISI 316 L steel) in which six tests were carried out with catalyst compositions containing various quantities of lithium, as set forth in Table 2 below.
Figure 6:
Figure 7:
Figure 8:
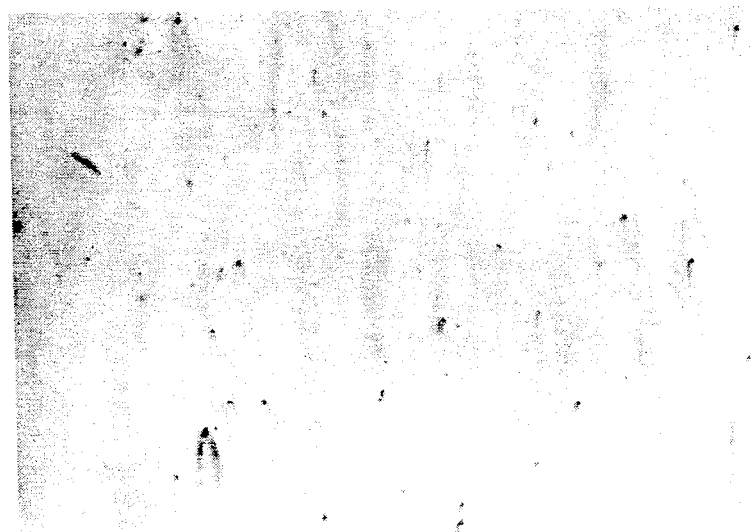
Figure 9:
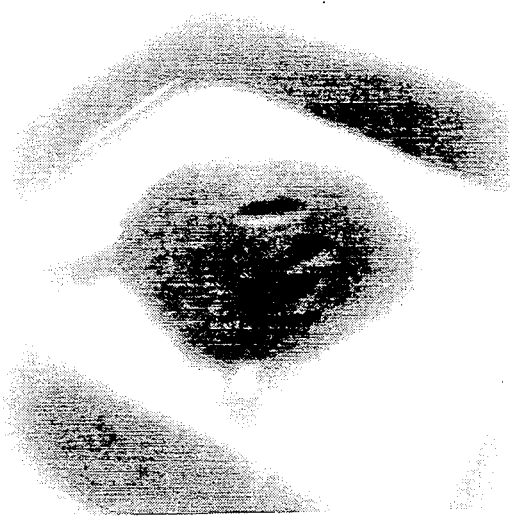
Figure 10:
Figure 11:
Figure 12:
Figure 13:

| TEST | 5 | 6 | 7 | 8 | 9 | 10 |
|---|---|---|---|---|---|---|
| AISI 316 L steel | FIG. 5 | FIG. 6 | FIG. 7 | FIG. 8 and 9 | FIG. 10 and 11 | FIG. 12 and 13 |

*Stable temperature profile in the reactor: the temperature of the fluid bed does not deviate by more than 2° C. from average temperature.
nd: not determined From the comparison of the results of the various tests it may be concluded that when operating above a certain lithium limit, the yield of 1,2-dichloroethane falls rapidly (tests 8 and 9) although the steel corrosion is weak but becomes unacceptable because of the adhesion and lumping of the catalyst particles (FIG. 9). From the results of the various tests it may also be concluded that when the lithium limits of the catalysts according to the invention are exceeded, the catalysts become unusable in practice because, in this case, high adhesion and high lumping are obtained (FIG. 10 and FIG. 12), and this makes corrosion measurements in an erosimeter impossible (FIG. 11 and FIG. 13).

We claim:

1. In a process for the oxychlorination of ethylene to 1,2-dichloroethane, the improvement comprising catalyzing the oxychlorination reaction by a catalyst composition consisting essentially of an alumina support on which there is deposited cupric chloride, magnesium chloride, and lithium chloride, wherein the lithium metal in the catalyst composition is employed in an atomic ratio relative to copper of between 0.0001 to 2 parts lithium per part copper.

2. The oxychlorination process according to claim 1, wherein said cupric chloride, magnesium chloride, and lithium chloride are employed in atomic ratios between 1:0.3–1:0.001–1.

3. The oxychlorination process of claim 1, wherein said cupric chloride, magnesium chloride, and lithium chloride are employed in atomic ratios of about 1:0.1:1.5.

4. The oxychlorination process of claim 1, wherein said cupric chloride, magnesium chloride, and lithium chloride are employed in atomic ratios of about 1:1.5:0.0001.

5. The oxychlorination process of claim 1, wherein said cupric chloride, magnesium chloride, and lithium chloride are employed in atomic ratios of about 1:1.5:1.5.

6. In a process for the oxychlorination of ethylene to 1,2-dichloroethane, the improvement comprising catalyzing the oxychlorination reaction by a catalyst composition consisting essentially of an alumina support, having a specific surface measured according to the B.E.T. method between 50 m$^2$/g and 250 m$^2$/g, on which there are deposited cupric chloride, magnesium chloride, and lithium chloride, wherein the lithium metal in the catalyst composition is employed in an atomic ratio relative to copper of between 0.0001 to 2 parts lithium:1 part copper.

7. In a process for the oxychlorination of ethylene to 1,2-dichloroethane, the improvement comprising catalyzing the oxychlorination reaction by a catalyst composition consisting essentially of an alumina support on which there is deposited cupric chloride, magnesium chloride, and lithium chloride employed in atomic ratios of about 1:0.1 to 1.5:0.0001 to 1.5.

8. The oxychlorination process set forth in claim 7, wherein the lithium metal in the catalyst composition is employed in an atomic ratio relative to copper of between 0.05 to 0.66 parts lithium per part copper.

9. The oxychlorination process set forth in claim 7, wherein said alumina support has a specific surface measured according to the B.E.T. method between about 50 m$^2$/g and 250 m$^2$/g.

10. The oxychorination process set forth in claim 7, wherein said cupric chloride, magnesium chloride, and lithium chloride are employed in atomic ratios between 1:0.3 to 1:0.0001 to 1.

11. The oxychlorination process set forth in claim 7, wherein said cupric chloride, magnesium chloride, and lithium chloride are employed in atomic ratios of about 1:0.1:1.5.

12. The oxychlorination process of claim 7, wherein said cupric chloride, magnesium chloride, and lithium chloride are employed in atomic ratios of about 1:1.5:0.0001.

13. The oxychlorination process set forth in claim 7, wherein said cupric chloride, magnesium chloride, and lithium chloride are employed in atomic ratios of about 1:1.5:1.5.

14. The oxychlorination process set forth in claim 7, wherein said cupric chloride, magnesium chloride, and lithium chloride are employed in atomic ratios of about 1:0.8:0.05.

* * * * *